US006939298B2

(12) United States Patent
Brown et al.

(10) Patent No.: US 6,939,298 B2
(45) Date of Patent: Sep. 6, 2005

(54) DEVICE AND METHOD FOR MONITORING AQUEOUS FLOW WITHIN THE EYE

(75) Inventors: Reay Brown, Atlanta, GA (US); Mary G. Lynch, Atlanta, GA (US)

(73) Assignee: GMP Vision Solutions, INC, Fort Lauderdale, FL (US)

( * ) Notice: Subject to any disclaimer, the term of this patent is extended or adjusted under 35 U.S.C. 154(b) by 120 days.

(21) Appl. No.: 10/376,793

(22) Filed: Feb. 28, 2003

(65) Prior Publication Data

US 2003/0232015 A1 Dec. 18, 2003

Related U.S. Application Data

(60) Provisional application No. 60/360,364, filed on Feb. 28, 2002.

(51) Int. Cl.[7] .............................................. A61B 5/00
(52) U.S. Cl. ........................................ 600/309; 600/398
(58) Field of Search ................................ 600/309–310, 600/318, 321, 398

(56) References Cited

U.S. PATENT DOCUMENTS

| | | | |
|---|---|---|---|
| 3,159,161 A | 12/1964 | Ness | |
| 3,863,623 A | 2/1975 | Trueblood et al. | 128/2 |
| 4,457,757 A | 7/1984 | Molteno | 604/294 |
| 4,573,778 A * | 3/1986 | Shapiro | 351/219 |
| 4,863,457 A | 9/1989 | Lee | 604/891 |
| 5,670,161 A | 9/1997 | Healy et al. | 424/426 |
| 5,922,304 A | 7/1999 | Unger | 424/9.3 |
| 5,991,697 A | 11/1999 | Nelson et al. | 702/49 |
| 6,006,128 A | 12/1999 | Izatt et al. | 600/476 |
| 6,039,691 A | 3/2000 | Walker | 600/452 |
| 6,059,728 A | 5/2000 | Ritter | 600/443 |
| 6,293,674 B1 | 9/2001 | Huang et al. | 351/221 |
| 6,315,981 B1 | 11/2001 | Unger | 424/9.323 |
| 6,375,642 B1 | 4/2002 | Grieshaber et al. | 604/294 |
| 6,494,857 B1 | 12/2002 | Neuhann | 604/8 |
| 6,533,768 B1 | 3/2003 | Hill | 604/521 |
| 6,681,127 B2 * | 1/2004 | March | 600/319 |
| 2002/0013546 A1 | 1/2002 | Grieshaber et al. | 604/28 |
| 2002/0072673 A1 * | 6/2002 | Yamamoto et al. | 600/452 |
| 2002/0133168 A1 | 9/2002 | Smedley et al. | 606/108 |
| 2002/0143284 A1 | 10/2002 | Tu et al. | 604/9 |
| 2002/0165478 A1 | 11/2002 | Gharib et al. | 604/8 |
| 2002/0169130 A1 | 11/2002 | Tu et al. | 514/12 |
| 2002/0188308 A1 | 12/2002 | Tu et al. | 606/167 |

FOREIGN PATENT DOCUMENTS

| | | |
|---|---|---|
| EP | 0 881 055 | 2/1998 |
| WO | 92/00112 | 1/1992 |
| WO | 92/19294 | 11/1992 |
| WO | 96/36377 | 11/1996 |
| WO | 00/52466 | 9/2000 |
| WO | WO 00/64393 | 11/2000 |
| WO | 01/78631 | 10/2001 |
| WO | 01/97727 | 12/2001 |
| WO | 02/36052 | 5/2002 |
| WO | 02/056758 | 7/2002 |
| WO | 02/074052 | 9/2002 |
| WO | 01/78656 | 10/2002 |
| WO | 02/080811 | 10/2002 |

OTHER PUBLICATIONS

Allen D. Beck and Mary G. Lynch, "360° Trabeculotomy for Primary Congenital Glaucoma," *Arch. Ophthalmol.* 113 (Sep. 1995), pp. 1200–1202.

* cited by examiner

*Primary Examiner*—Eric F. Winakur
*Assistant Examiner*—Matthew Kremer
(74) *Attorney, Agent, or Firm*—Lott & Friedland, P.A.

(57) ABSTRACT

The present invention provides a device and method for monitoring the flow of aqueous humor within the eye. The invention provides that the aqueous flow rate and/or pattern within the anatomical structures of the eye can be determined by monitoring a traceable component. Such determination provides diagnostic indications of the degree and location of ocular disease associated with aqueous outflow, such as glaucoma, and can further provide post-treatment indications of effectiveness.

21 Claims, 1 Drawing Sheet

DEVICE AND METHOD FOR MONITORING
AQUEOUS FLOW WITHIN THE EYE

CROSS REFERENCE TO RELATED
APPLICATIONS

The present invention claims the priority benefit of U.S. Provisional Patent Application Ser. No. 60/360,364 filed Feb. 28, 2002, the entire contents of which are hereby incorporated by reference.

BACKGROUND OF THE INVENTION

1. Field of the Invention

The present invention is generally directed to a device and method for measuring, monitoring and recording aqueous outflow from, the eye and relates to a method of delineating the pattern of aqueous outflow and the location and extent of resistance to outflow in glaucoma. Furthermore, the device and method can be utilized to monitor the effect various glaucoma therapies have on the pattern of outflow in glaucoma.

2. Background Art

Glaucoma is a significant public health problem, because glaucoma is a major cause of blindness. The blindness that results from glaucoma involves both central and peripheral vision and has a major impact on an individual's ability to lead an independent life.

Glaucoma is an optic neuropathy (a disorder of the optic nerve) that usually occurs in the setting of an elevated intraocular pressure. The pressure within the eye increases and this is associated with changes in the appearance ("cupping") and function ("blind spots" in the visual field) of the optic nerve. If the pressure remains high enough for a long enough period of time, total vision loss occurs. High pressure develops in an eye because of an internal fluid imbalance.

The eye is a hollow structure that contains a clear fluid called "aqueous humor." Aqueous humor is formed in the posterior chamber of the eye by the ciliary body at a rate of about 2.5 microliters per minute. The fluid, which is made at a fairly constant rate, then passes around the lens, through the pupillary opening in the iris and into the anterior chamber of the eye. Once in the anterior chamber, the fluid drains out of the eye through two different routes. In the "uveoscleral" route, the fluid percolates between muscle fibers of the ciliary body. This route accounts for approximately ten percent of the aqueous outflow in humans. The primary pathway for aqueous outflow in humans is through the "canalicular" route that involves the trabecular meshwork and Schlemm's canal.

The trabecular meshwork and Schlemm's canal are located at the junction between the iris and the sclera. This junction or corner is called "the angle." The trabecular meshwork is a wedge-shaped structure that runs around the circumference of the eye. It is composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. Schlemm's canal is adjacent to the trabecular meshwork. The outer wall of the trabecular meshwork coincides with the inner wall of Schlemm's canal. Schlemm's canal is a tube-like structure that runs around the circumference of the cornea.

The aqueous fluid travels through the spaces between the trabecular beams, across the inner wall of Schlemm's canal and into the canal. From Schlemm's canal, the fluid flows through a series of about 25 collecting channels that drain into aqueous veins. The aqueous veins, which contain a mixture of aqueous fluid and venous blood, drain into the episcleral venous system. The episcleral venous system forms a plexus of blood vessels on the surface of the eye.

In a normal situation, aqueous production is equal to aqueous outflow and intraocular pressure remains fairly constant in the 15 to 21 mm Hg range. In glaucoma, the resistance through the canalicular outflow system is abnormally high. The increased resistance is believed to be present along the outer aspect of trabecular meshwork and the inner wall of Schlemm's canal. It is believed that the distal outflow system (Schlemm's canal, collecting channels, aqueous veins, episcleral plexus) is normal.

In primary open angle glaucoma, which is the most common form of glaucoma, the abnormal resistance is believed to be along the outer aspect of trabecular meshwork and the inner wall of Schlemm's canal. It is believed that an abnormal metabolism of the trabecular cells leads to an excessive build up of extracellular materials or a build up of abnormally "stiff" materials in this area. Primary open angle glaucoma accounts for approximately eighty-five percent of all glaucoma. Other forms of glaucoma (such as angle closure glaucoma and secondary glaucomas) also involve decreased outflow through the canalicular pathway but the increased resistance is from other causes such as mechanical blockage, inflammatory debris, cellular blockage, etc.

With the increased resistance, the aqueous fluid builds up because it cannot exit fast enough. As the fluid builds up, the intraocular pressure (IOP) within the eye increases. The increased IOP compresses the axons in the optic nerve and also may compromise the vascular supply to the optic nerve. The optic nerve carries vision from the eye to the brain. Some optic nerves seem more susceptible to IOP than other eyes. While research is investigating ways to protect the nerve from an elevated pressure, the only therapeutic approach currently available in glaucoma is to reduce the intraocular pressure.

The clinical treatment of glaucoma is approached in a stepwise fashion. Medication often is the first treatment option. Administered topically or systemically, glaucoma medications work either to reduce aqueous production or to enhance aqueous outflow. When medication fails to adequately reduce the pressure, laser trabeculoplasty often is performed. In laser trabeculoplasty, thermal energy from a laser is applied to a number of noncontiguous spots in the trabecular meshwork. It is believed that the laser energy stimulates the metabolism of the trabecular cells in some way and changes the outflow resistance. If laser trabeculoplasty fails to adequately reduce the pressure, surgery is performed. Currently, all surgical procedures involve the creation of a hole in the sclera that allows aqueous fluid to collect on the surface of the eye.

Newer surgical methods are being developed that target the abnormal area of resistance in the trabecular meshwork. These methods, which include trabeculotomy, goniotomy, goniocurettage, excimer laser trabecular ablation and the GMP BiDirectional Glaucoma shunt (described in WO 00/64393), aim to eliminate the area of resistance and allow aqueous to gain access to the distal outflow system.

The current understanding of the human outflow system is based primarily on histologic study of cadaver eyes and indirect physiological measurements. For instance, the presence and in vitro appearance of the distal outflow system can be demonstrated by injecting tracers (dye, blood, particles)

into Schlemm's canal. However, the in vivo behavior of the plexus is unknown. Likewise, the speed of aqueous outflow can be indirectly measured through fluorophotometry. With fluorophotometry, fluorescein dye is applied to the surface of the eye, absorbed into the anterior chamber and then its disappearance from the eye measured with a photometer. However, the pattern and extent of aqueous outflow cannot be measured with this technique.

Some investigators believe that once aqueous humor reaches Schlemm's canal, the fluid travels circumferentially to exit the eye through the collecting channel that offers the least resistance. Others believe that aqueous humor passes quickly through Schlemm's canal and exits the eye through the adjacent collecting channel with minimal circumferential flow. Thus, the pattern of aqueous outflow from a normal eye remains controversial.

Furthermore, some investigators believe that in glaucoma, the resistance through the trabecular meshwork gradually and uniformly increases, until a threshold of resistance is reached after which intraocular pressure increases. Other investigators believe that the abnormal outflow resistance is segmental, affecting only certain areas of the trabecular meshwork. According to this premise, the pattern of segmental resistance would vary among glaucoma patients. Thus, the location and extent of resistance in glaucoma also remains controversial.

Currently, there is no diagnostic tool to analyze the pattern of aqueous outflow or the location of abnormal resistance for an individual patient. Furthermore, there is no diagnostic tool to measure the effect that intervention (medication, laser, surgery) has on aqueous outflow.

SUMMARY OF THE INVENTION

The present invention is directed to a novel method and device associated therewith for monitoring aqueous outflow from the eye by administering to the eye a traceable component, monitoring the flow of the traceable component through an anatomical structure of the eye associated with aqueous humor flow, and thereby determining the aqueous humor flow in the anatomical structure of the eye. The present invention can delineate the pattern of aqueous outflow for individual patients and help to direct a therapy. The present invention elucidates the manner by which glaucoma therapies work to lower intraocular pressure.

The present invention further provides a method of determining the pattern and extent of aqueous outflow in the eye, comprising monitoring the flow of aqueous humor in an anatomical structure of the eye associated with aqueous humor flow. The present invention further provides a method of locating an obstruction in an eye of a patient with glaucoma, comprising determining the location and extent of resistance in the flow of aqueous humor in an anatomical structure of the eye associated with aqueous humor flow. An additional method encompassed by the present invention is a method of monitoring the response to intervention in a glaucoma patient, comprising determining the location and extent of resistance in the flow of aqueous humor in an anatomical structure of the eye associated with aqueous humor flow.

The present invention encompasses a kit for the determination of the pattern and extent of aqueous outflow in the eye, comprising a traceable component for administration to the eye and instructions for the use of the traceable component for determining the pattern and extent of aqueous outflow in the eye, comprising monitoring the flow of aqueous humor in an anatomical structure of the eye associated with aqueous humor flow. In another embodiment, the kit comprises a traceable component for administration to the eye and instructions for the use of the traceable component for locating an obstruction in an eye of a patient with glaucoma, comprising determining the location and extent of resistance in the flow of aqueous humor in an anatomical structure of the eye associated with aqueous humor flow. In another embodiment, the kit comprises a traceable component for administration to the eye and instructions for the use of the traceable component for monitoring the response to intervention in a glaucoma patient, comprising determining the location and extent of resistance in the flow of aqueous humor in an anatomical structure of the eye associated with aqueous humor flow.

DETAILED DESCRIPTION OF THE INVENTION

Figure 1:
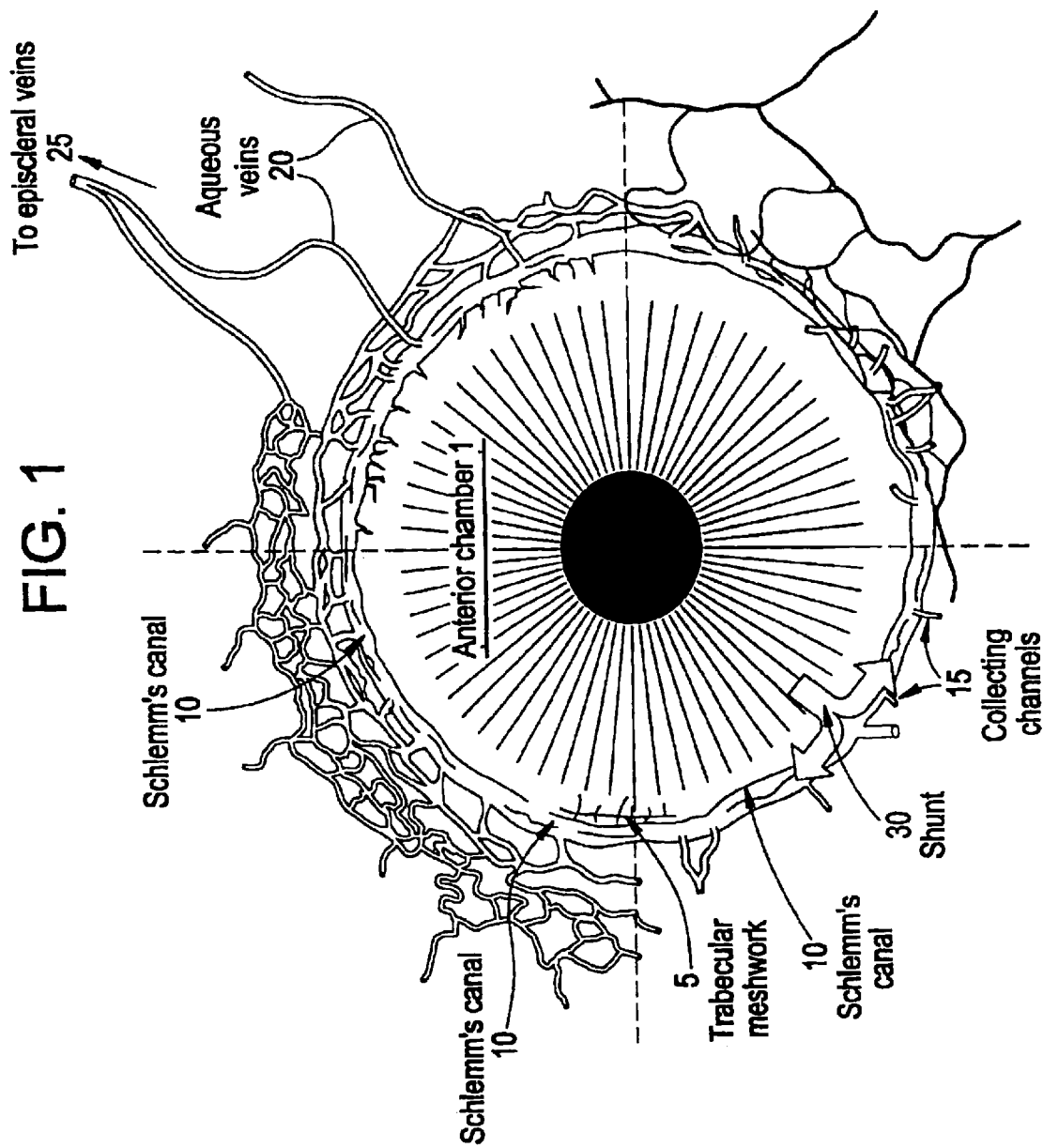
FIG. 1 is an illustration showing the outflow plexus of the eye through the anterior chamber, trabecular meshwork, Schlemm's canal, collecting channels, aqueous veins, and episcleral veins.

The present invention provides devices and methods for monitoring aqueous humor flow within the eye. One method comprises administering to an eye a traceable component, monitoring the flow of the traceable component through an anatomical structure of the eye associated with aqueous humor flow, and determining the aqueous humor flow in the anatomical structure of the eye. The invention provides devices particularly adapted to practice the methods as described below.

The present invention further provides a method of determining the pattern and extent of aqueous outflow in the eye, comprising monitoring the flow of aqueous humor in an anatomical structure of the eye associated with aqueous humor flow. The present invention further provides a method of locating an obstruction in an eye of a patient with glaucoma, comprising determining the location and extent of resistance in the flow of aqueous humor in an anatomical structure of the eye associated with aqueous humor flow. An additional method encompassed by the present invention is a method of monitoring the response to intervention in a glaucoma patient, comprising determining the location and extent of resistance in the flow of aqueous humor in an anatomical structure of the eye associated with aqueous humor flow.

The present invention encompasses a kit for the determination of the pattern and extent of aqueous outflow in the eye, comprising a traceable component for administration to the eye and instructions for the use of the traceable component for determining the pattern and extent of aqueous outflow in the eye, comprising monitoring the flow of aqueous humor in an anatomical structure of the eye associated with aqueous humor flow. In another embodiment, the kit comprises a traceable component for administration to the eye and instructions for the use of the traceable component for locating an obstruction in an eye of a patient with glaucoma, comprising determining the location and extent of resistance in the flow of aqueous humor in an anatomical structure of the eye associated with aqueous humor flow. In another embodiment, the kit comprises a traceable component for administration to the eye and instructions for the use of the traceable component for monitoring the response to intervention in a glaucoma patient, comprising determining the location and extent of resistance in the flow of aqueous humor in an anatomical structure of the eye associated with aqueous humor flow.

In one embodiment of the above methods and kits, monitoring the flow of aqueous humor comprises the steps of (1) measuring the flow of aqueous humor at a first anatomical structure of the eye associated with aqueous humor flow; and (2) comparing the flow of aqueous humor at the first anatomical structure to the flow of aqueous humor at a second anatomical structure of the eye associated with aqueous humor flow to thereby monitor the flow of aqueous humor. In another embodiment, monitoring the flow of aqueous humor comprises the steps of (1) measuring the flow of aqueous humor at a first location in an anatomical structure of the eye associated with aqueous humor flow; and (2) comparing the flow of aqueous humor at the first location in an anatomical structure of the eye to the flow of aqueous humor at a second location in the same anatomical structure of the eye. In another embodiment, monitoring the flow of aqueous humor comprises the steps of (1) measuring the flow of aqueous humor at a first location in an anatomical structure of the eye associated with aqueous humor flow; and (2) comparing the flow of aqueous humor at the first location to the flow of aqueous humor at the first location after a period of time.

In another embodiment of the above methods and kits, determining the location and extent of resistance in the flow of aqueous humor comprises the steps of (1) measuring the flow of aqueous humor at a first anatomical structure of the eye associated with aqueous humor flow; and (2) comparing the flow of aqueous humor at the first anatomical structure of the eye to the flow of aqueous humor at a second anatomical structure of the eye associated with aqueous humor flow to thereby determine the location and extent of resistance in the flow of aqueous humor. In another embodiment, determining the location and extent of resistance in the flow of aqueous humor comprises the steps of (1) measuring the flow of aqueous humor at an anatomical structure of the eye associated with aqueous humor flow; and (2) comparing the flow of aqueous humor at the anatomical structure of the eye to the flow of aqueous humor at a different location in the same anatomical structure of the eye to thereby determine the location and extent of resistance in the flow of aqueous humor. In another embodiment, determining the location and extent of resistance in the flow of aqueous humor comprises the steps of (1) measuring the flow of aqueous humor at one location in a first anatomical structure of the eye associated with aqueous humor flow; and (2) comparing the flow of aqueous humor at the one location to the flow of aqueous humor at the same one location after a period of time to thereby determine the location and extent of resistance in the flow of aqueous humor.

The invention provides that the presence, rate, volume and/or components of the aqueous humor flow in the eye can be determined relative to observations of the monitored flow of traceable component. Preferably, the monitoring step provides visualization of the aqueous flow path within the various anatomical structures within the eye associated with aqueous humor flow. Monitoring can be performed as of any point in time or over a course of time, depending upon the method chosen, as described below. If the monitoring occurs over a period of time, the measurements may be taken during the same monitoring session, or they may be taken within minutes, within hours, within days, or within months or years of each other. The devices of the present invention can perform the monitoring function alone, or both the administration and monitoring functions together.

The method can be performed along any desired anatomical structure within the eye associated with the aqueous humor flow path, such as through the anterior chamber, trabecular meshwork, Schlemm's canal, collecting channels, aqueous veins, and episcleral veins, as seen in FIG. 1. For example, monitoring may be of the aqueous humor flow path or rate from the anterior chamber to the aqueous veins, or from the anterior chamber to Schlemm's canal, or from Schlemm's canal to the -episcleral veins, or between any desired anatomical reference points associated with the eye within which aqueous humor flows. The method of the invention can be referred to as "canalagraphy."

Furthermore, the invention provides methods for comparing the monitored flow rates between different anatomical structures associated with the eye for a determination of where aqueous humor flow is inhibited or induced. Alternatively, the comparison may be between similar anatomical structures within different radial segments of the eye, such as for a determination of the circumferential path of aqueous within Schlemm's canal or a diagnostic determination of the location of aqueous outflow inhibition. Alternatively, the comparison be may between the same anatomical structure in the eye taken at different points in time to evaluate whether aqueous flow is inhibited or induced in response to the progression of glaucoma, or in response to an intervention to treat glaucoma. As used herein, the term "intervention") refers to a procedure to treat glaucoma, and the intervention is selected from the group consisting of medication, surgery, and laser treatment. In one embodiment, the intervention is a surgical implant.

The invention can be used in conjunction with a surgical implant, such as a shunt device described WO 00/64393 used to divert aqueous humor in the eye from the anterior chamber into Schlemm's canal. Such a device comprises a distal portion having at least one terminal aspect sized and shaped to be circumferentially received within a portion of Schlemm's canal, and a proximal portion having at least one terminal aspect sized and shaped to be received within the anterior chamber of the eye, wherein the device permits fluid communication between the proximal portion in the anterior chamber to the distal portion in Schlemm's canal. Therefore, the present methods and devices can be used in a diagnostic determination of where such a shunt or other therapeutic intervention may be most needed within the eye, or may be used after such therapeutic intervention for a determination of the resulting aqueous humor outflow therethrough.

In certain embodiments of the present invention, the flow of aqueous humor is determined relative to observation of a monitored flow of a traceable component. In one embodiment, the traceable component is administered topically to the eye. In another embodiment, the traceable component is administered directly into the anterior chamber. In another embodiment, the traceable component is administered directly into an anatomical structure of the eye associated with aqueous humor flow, selected from the group comprising an anterior chamber, a trabecular meshwork, a Schlemm's canal, a collecting channel, an aqueous vein, and an episcleral vein. In certain other embodiments of the present invention, monitoring the flow of aqueous humor is performed without the administration of an exogenous traceable component.

Depending upon the type of traceable component used, the present invention can be used to diagnose the causes of improper resistance to the aqueous outflow system. This may be achieved by a determination of the location of aqueous outflow resistance or an observable interaction between diseased tissues or pathogenic markers and the traceable component, such as antibody-antigen binding. The aqueous imaging within the structures of the eye can also be used co-operatively for observations of surgical and therapeutic manipulations of the anatomical structures within the eye associated with aqueous flow.

The invention contemplates many different embodiments for administering the traceable component to the eye. The traceable component can be administered into the eye topically through the cornea, and entry may be facilitated by iontophoresis or electroporation for example. Alternatively, the traceable component can be administered directly into the anterior chamber or other anatomical structure within the eye, such as through a syringe. Selection of the traceable component will depend upon the corresponding monitoring system, as can be routinely determined by those of skill in the art.

Many techniques are known for in vivo fluid and tissue monitoring which can be adapted for monitoring a traceable agent within the eye. For example, colored dyes can be introduced into the anterior chamber and visualized upon exiting the episcleral veins over the course of a monitored period of time to determine overall flow rate. Radiopaque dyes detectable by x-rays can be used for more specific aqueous flow pattern visualization within the eye. Similarly, fluorescing compounds used in association with a fluoroscopic image intensifier can be used for aqueous flow pattern visualization within the eye. Radioisotopes can be used as traceable components for aqueous flow pattern visualization within the eye. Infrared detectors can alternatively be used with a traceable component having a thermal profile distinguishable over the tissues of the eye.

Optionally, an ultrasound system can be used to monitor the flow of a traceable component through the eye, such as in kinetic acoustic ocular examination described in U.S. Pat. No. 6,039,691, or a three-dimensional ultrasound imaging probe described in U.S. Pat. No. 6,059,728. Monitoring technology further includes optical Doppler tomography as described in U.S. Pat. No. 5,991,697 that allows in vivo imaging of circulation and tissue structure. Alternatively, a velocity-indicating image can be generated with optical coherence tomography as described in U.S. Pat. No. 6,006,128. Relatedly, an Optical Coherence Tomography system (U.S. Pat. No. 6,293,674 to Carl Zeiss Opthalmic Systems, Dublin, Calif.), using light rather than ultrasound, can be used to scan the eye for the flow of traceable component. Furthermore, magnetic resonance imaging technologies, such as those using gaseous precursor filled microspheres as contrasting agents described in U.S. Pat. No. 6,315,981 and U.S. Pat. No. 5,922,304 can be used to observe the route and amount of traceable component flowing through the eye in association with aqueous humor. It is to be understood that in embodiments where the monitoring technique requires no exogenous traceable element, such as in Optical Coherence Tomography and infrared, the method does not require a separate step for administering the traceable element.

Each of the patents cited above are hereby incorporated by reference in their entireties. While the above-described embodiments are exemplary, the invention contemplates a wide variety of devices and methods for monitoring the aqueous humor outflow within the eye. The above-described embodiments are therefore not intended to be limiting to the scope of the equivalents thereof.

EXAMPLES

In evaluating the effectiveness of the bi-directional shunt implant device described WO 00/64393, the following system was established to monitor the distal outflow system in a matched pair of human cadaver eyes. The intraocular pressure was maintained at a physiologic level, and then food coloring was instilled into the anterior chamber. The outflow of food coloring was monitored from the eye, judging the location and time of its first appearance, the pattern of fill of the episcleral vessels and the time it took for the dye to saturate the system. These measurements provided information on what was happening to the outflow system before and after implantation of the shunt.

In the first this eye, food coloring was injected into the anterior chamber, and the time it took for the dye to appear in the aqueous veins was monitored. The dye appeared in several aqueous veins simultaneously and its first appearance was at about 11 seconds. Then, the episcleral vessels began to become colored, and it took about 36 seconds for saturation to occur, as defined by when the dye seemed to be flowing freely out of the system.

In the fellow eye, a bi directional shunt was implanted superiorly within Schlemm's canal. In addition, a suture was placed at the limbus that effectively closed the shunting arm on the right side. Therefore, the food coloring was free to flow down the left arm, but restricted from flowing down the right arm. Food coloring was injected into the anterior chamber and monitored. First, the dye exited at the aqueous vein nearest to the left side of the shunt. This first appearance occurs at about 10 seconds. Next, the contiguous aqueous veins became colored sequentially as opposed to colored simultaneously. The last area to become colored was adjacent to the obstructed arm on the right side. Finally, with shunting of the aqueous fluid, full saturation occurred at about 17 seconds, which was about half the time as in the eye without the shunt. This example indicates that in a normal eye, aqueous reaches the entire distal outflow system simultaneously. After implanting the shunt, fluid seems to reach the outflow system faster and in a more sequential pattern.

We claim:

1. A method of determining a pattern and extent of aqueous outflow in the eye, comprising monitoring the flow of aqueous humor in an anatomical structure of the eye associated with aqueous humor flow, wherein monitoring the flow of aqueous humor comprises the steps of:
   a) measuring the flow of aqueous humor at a first anatomical structure of the eye associated with aqueous humor flow; and
   b) comparing the flow of aqueous humor at the first anatomical structure to the flow of aqueous humor at a second anatomical structure of the eye associated with aqueous humor flow to thereby monitor the flow of aqueous humor wherein the flow of aqueous humor is determined relative to observation of a monitored flow of a traceable component.

2. The method of claim 1, wherein the traceable component is administered topically.

3. The method of claim 1, wherein the traceable component is administered directly into the anterior chamber.

4. The method of claim 1, wherein the traceable component is administered directly into an anatomical structure of the eye associated with aqueous humor flow, selected from the group comprising an anterior chamber, a trabecular meshwork, a Schlemm's canal, a collecting channel, an aqueous vein, and an episcleral vein.

5. The method of claim 1, wherein the traceable component is selected from the group consisting of a colored dye, a radiopaque dye, a fluorescing compound, a radioisotope, and a gaseous precursor filled microsphere.

6. The method of claim 1, wherein monitoring the flow of aqueous humor is performed without the administration of an exogenous traceable component.

7. The method of claim 1, wherein the monitoring step identifies an aqueous outflow obstruction in an eye of a patient with glaucoma.

8. The method of claim 1, wherein the monitoring step identifies a response to therapeutic intervention in an eye of a patient with glaucoma.

9. A method of determining a pattern and extent of aqueous outflow in the eye, comprising monitoring the flow of aqueous humor in an anatomical structure of the eye associated with aqueous humor flow, wherein monitoring the flow of aqueous humor comprises the steps of:
   a) measuring the flow of aqueous humor at a first location in an anatomical structure of the eye associated with aqueous humor flow; and
   b) comparing the flow of aqueous humor at the first location in an anatomical structure of the eye to the flow of aqueous humor at a second location in the same anatomical structure of the eye
   wherein the flow of aqueous humor is determined relative to observation of a monitored flow of a traceable component.

10. The method of claim 9, wherein the traceable component is administered topically.

11. The method of claim 9, wherein the traceable component is administered directly into the anterior chamber.

12. The method of claim 9, wherein the traceable component is administered directly into an anatomical structure of the eye associated with aqueous humor flow, selected from the group comprising an anterior chamber, a trabecular meshwork, a Schlemm's canal, a collecting channel, an aqueous vein, and an episcleral vein.

13. The method of claim 9, wherein the traceable component is selected from the group consisting of a colored dye, a radiopaque dye, a fluorescing compound, a radioisotope, and a gaseous precursor filled microsphere.

14. The method of claim 9, wherein monitoring the flow of aqueous humor is performed without the administration of an exogenous traceable component.

15. The method of claim 9, wherein the monitoring step identifies an aqueous outflow obstruction in an eye of a patient with glaucoma.

16. The method of claim 9, wherein the monitoring step identifies a response to therapeutic intervention in an eye of a patient with glaucoma.

17. A method of determining a pattern and extent of aqueous outflow in the eye, comprising monitoring the flow of aqueous humor in an anatomical structure of the eye associated with aqueous humor flow, wherein monitoring the flow of aqueous humor comprises the steps of:
   a) measuring the flow of aqueous humor at a first location in an anatomical structure of the eye associated with aqueous humor flow; and
   b) comparing the flow of aqueous humor at the first location to the flow of aqueous humor at the first location after a period of time,
   wherein the flow of aqueous humor is determined relative to observation of a monitored flow of a traceable component, and wherein the traceable component is administered directly into the anterior chamber.

18. The method of claim 17, wherein the traceable component is selected from the group consisting of a colored dye, a radiopaque dye, a fluorescing compound, a radioisotope, and a gaseous precursor filled microsphere.

19. The method of claim 17, wherein monitoring the flow of aqueous humor is performed without the administration of an exogenous traceable component.

20. The method of claim 17, wherein the monitoring step identifies an aqueous outflow obstruction in an eye of a patient with glaucoma.

21. The method of claim 17, wherein the monitoring step identifies a response to therapeutic intervention in an eye of a patient with glaucoma.

* * * * *